United States Patent [19]  [11] 4,159,896
Levine et al.  [45] Jul. 3, 1979

[54] ENHANCEMENT OF SEPARATION OF CELL LAYERS IN CENTRIFUGED BLOOD SAMPLE

[75] Inventors: Robert A. Levine, Guilford; Stephen C. Wardlaw, Branford, both of Conn.

[73] Assignee: James V. Massey, III, Trumball, Conn. ; a part interest

[21] Appl. No.: 910,807

[22] Filed: May 30, 1978

Related U.S. Application Data

[63] Continuation-in-part of Ser. No. 758,065, Jan. 10, 1977, abandoned.

[51] Int. Cl.² .......................... A61B 5/14; G01N 33/16
[52] U.S. Cl. ..................................... 23/230 B; 73/444; 210/83
[58] Field of Search ............... 23/230 B; 73/444; 61.4; 210/83, DIG. 23, 24, 94; 128/2 F, 2 G, DIG. 5

[56] References Cited

U.S. PATENT DOCUMENTS

| 2,102,785 | 12/1937 | Brooks | 23/230 B |
| 2,725,782 | 12/1955 | Worley | 23/230 B X |
| 3,684,450 | 8/1972 | Adler et al. | 23/230 B |
| 3,914,985 | 10/1975 | Von Bakers | 23/230 B X |
| 3,931,018 | 1/1976 | North, Jr. | 210/DIG. 23 |
| 3,965,889 | 6/1976 | Sacks | 128/2 F |
| 4,027,660 | 6/1977 | Wardlaw et al. | 210/DIG. 23 |
| 4,077,396 | 3/1978 | Wardlaw et al. | 128/2 G |
| 4,082,085 | 4/1978 | Wardlaw et al. | 128/2 G |

Primary Examiner—Michael S. Marcus
Attorney, Agent, or Firm—William W. Jones

[57] ABSTRACT

An improvement in the degree of separation of constituent cell layers in a centrifuged sample of human blood is achieved by decreasing the natural water content of the red blood cells to increase their density or specific gravity. Thus the red cell layer packs more tightly and separates more completely from the next lighter cell layer adjacent thereto, i.e., the granulocyte layer.

7 Claims, 1 Drawing Figure

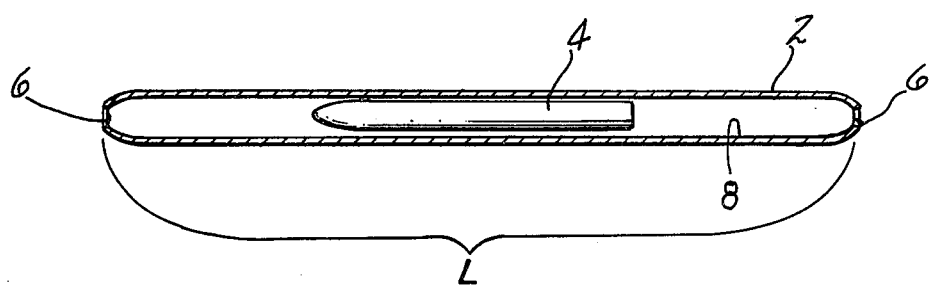

ENHANCEMENT OF SEPARATION OF CELL LAYERS IN CENTRIFUGED BLOOD SAMPLE

This application is a continuation-in-part of U.S. patent application Ser. No. 758,065, filed Jan. 10, 1977, now abandoned.

This invention relates to techniques for making approximate white cell blood counts and granulocyte-/mononuclear ratio cell counts, and particularly to a technique for enhancement of the separation of individual layers in a centrifuged blood sample. This invention is related to and useful in conjunction with the techniques of blood testing disclosed in U.S. Pat. No. 4,027,660, issued June 7, 1977.

The techniques disclosed in the referenced patent relate to the measurement of approximate white cell blood counts, platelet counts, and granulocyte-/mononuclear ratio counts and to methods and paraphenalia used in such measurements. Generally the techniques involve the centrifugation of a blood sample in a tube which contains a volume-occupying insert which floats upon the red cell layer and axially elongates the buffy coat or white cell and platelet layer by a multiple of four or more. The blood sample being tested is anti-coagulated blood. The order of layering by density or specific gravity of an anticoagulated human blood sample in this technique from lightest constituent to heaviest constituent is plasma, followed by platelets, followed by mononuclear cells, followed by granulocytes and finally red cells. In the type of system described in the referenced patent, separation of each layer is usually adequate for visual identification and gives relatively sharp interface delineation with the exception of the interface between the granulocyte layer and the red cell layer, which is often hazy and ill-defined in appearance.

The reason for this is that, in some blood samples, the difference between the density or specific gravity of the individual granulocyte cells and the youngest and lightest red cells is not great enough to provide a sharp demarcation line between these adjacent cell layers. This lack of a sharp demarcation line is the direct result of the lighter young red cells tending to intermingle with the granulocyte cells near the common interface and causes difficulties in accurately measuring the extent of the red cell layer and the granulocyte layer. This invention is designed to eliminate these difficulties by increasing the density difference between the granulocytes and the youngest red cells thereby ensuring that the younger red cells pack tightly into the remaining red cell mass thereby providing a sharp line of demarcation between these layers.

The various cellular components of blood can be thought of as "sacks" of protein, each surrounded by membranes which are freely permeable to water and selectively permeable to other substances. Since the density or specific gravity of the blood cells depends primarily on the ratio of intracellular water to protein, changing this ratio will change the density or specific gravity of the cells. We have discovered that the demarcation line between the granulocyte layer and the red cell layer in a sample of centrifuged anticoagulated blood can be sharpened or better defined by adding a substance to the blood sample which effectively increases the density of the red cells without significantly affecting the density of the granulocytes. The particular substance added to the blood sample is a substance which extracts water from the red cells, thus rendering them more dense, but does not significantly affect the intracellular water-to-protein ratio of the granulocytes or other cell types and thus does not significantly change their natural density.

We theorize that the mechanism by which the substance operates is as follows. The membranes surrounding individual red cells are, in general, less permeable to substances than are the membranes surrounding the other individual cell types in blood. Thus, a substance is added to the blood sample which freely moves through each of the cell type membranes except the red cell membrane. The addition of such a substance causes intracellular water to be removed from the red cells by the process of osmosis. This removal of intracellular water from the red cells increases their density or specific gravity. At the same time, since the added substance moves freely through the remainder of the blood cell membranes, substantially no intracellular water is removed therefrom, thus their density or specific gravity is not increased. The overall result is that the "densified" red cells, including the young red cells, pack more tightly, but the remaining cells, including the granulocytes, pack in substantially the same manner as they do without the addition of the substance. Thus, the young red cells pack tightly into the red cell mass and no longer obscure the demarcation line between the red cells and the granulocytes.

The substance which we prefer to use for selectively altering the specific gravity of the red blood cell constituent in the manner specified above is potassium oxalate. One reason for preferring potassium oxalate is that, in addition to its excellent ability to desirably alter the specific gravity of the red blood cell types, it is also an anti-coagulant for the blood. Thus, it performs a dual function. When potassium oxalate is used merely for its anti-coagulant function, it is used in a concentration of about 200 mg/dl of solution. This concentration will cause about an 8% shrinkage of the red cells due to a loss of intracellular water whereby the density or specific gravity of the red cells is increased. This "merely anticoagulating" concentration of 200 mg/dl is not sufficient to provide the degree of separation of red cells from white cells which we require, however. We prefer to use a potassium oxalate concentration in the range of about 400 mg/dl to about 600 mg/dl solution to provide the required degree of cell separation. This increased concentration does not adversely affect the ability of the potassium oxalate to anticoagulate the blood sample. Furthermore, this increased concentration of potassium oxalate does not significantly increase the density of a significant portion of the white cells in a majority of blood samples, whereby good separation can be achieved without the need to make any mathematical corrections for the white cell layer thicknesses observed. The increased density of the red cells due to the addition of greater than conventional concentrations of potassium oxalate results in a more compacted red cell mass than usually observed; however, the hematocrit reading for the blood sample can still be made by mathematically correcting the observed red cell column height. It should be noted that the red cell densification result of adding even a conventional 200 mg/dl solution of potassium oxalate to a blood sample for anti-coagulating purposes has, in the past, resulted in that particular anticoagulant not being used in blood tests which include a hematocrit count. Instead, other non-densifying anti-coagulants, such as heparin, have been used.

Other reagents which will provide an improved separation line between the red cells and the granulocytes are lithium lactate and sodium citrate. Of the three reagents, potassium oxalate is most preferred, lithium lactate is next preferred, and sodium citrate is least preferred. Compounds noted which are operable to selectively render the red cells more dense while not affecting the white cells are compounds which have an organic anion in combination with a freely soluble metallic cation.

A specific example of the use of potassium oxalate mixture which is preferred is as follows. Blood from a donor was divided into 0.5 ml. aliquots. To one of the aliquots was added sufficient potassium oxalate to raise the whole blood osmolality by 50 milli-osmoles/liter. In making this calculation, all cells were considered as producing an osmotic effect, and complete disassociation was assumed. The blood was then drawn into capillary tubes and spun down. A control sample with no additives showed fair separation between the red cell and granulocyte layers. The sample containing the potassium oxalate showed excellent separation between the red cell and granulocyte layers.

The additive is preferably deposited in a dry form on the inside surface of the capillary tube in which the testing procedure is carried out by means of freeze drying. Other coating procedures can be used, however.

The accompanying drawing illustrates a preferred embodiment of a capillary testing tube formed in accordance with the invention. The drawing, which is a sectional view of a capillary tube formed in accordance with the invention, discloses a capillary tube 2 having a plastic volume-occupying insert 4 in the form of a right cylinder with an upper, inwardly tapered end portion. The insert 4 can be prevented from falling out of the tube bore by crimping the ends of the tube inwardly, as at 6. Alternatively, a blood-soluble adhesive can be used to hold the insert 4 in place. Gum acacia is such an adhesive. Substantially the entire length L of the tube bore wall 8 is preferably coated with a dry layer of the additive which increases the density of the red cells but does not significantly increase the density of the white cells.

The tube assembly shown is used by drawing the blood sample into it. The blood flowing into the tube dissolves the dry coating of the additive and causes it to go into solution in the blood. It is then free to perform its intended function.

It will be appreciated that the method of this invention can be performed by adding the reagent, preferably potassium oxalate, to the blood sample before the sample is drawn into the capillary tube.

While a preferred embodiment of the invention has been disclosed heretofore, it is not intended to limit the invention otherwise than as required by the appended claims.

What is claimed is:

1. A method for clarifying the interface between an enhanced white cell layer and the red cell layer in a centrifuged sample of blood including the step of adding to the blood sample an additive in an amount effective to prevent any immature red cells from being suspended in the adjacent white cell layer by increasing the specific gravity of the red cells without significantly altering the specific gravity of a significant number of the white cells.

2. The method of claim 1 wherein the additive is one which effects removal of water from the individual red cells without significantly effecting removal of water from the white cells.

3. The method of claim 1 wherein the additive is potassium oxalate.

4. A method for clarifying the interface between the red cell layer and an enhanced layer of white cells in a blood sample comprising the steps of drawing a blood sample into a capillary tube; adding to the sample a compound in an amount effective to increase the specific gravity of the red cells thereby preventing any immature red cells from being suspended in the adjacent white cell layer without significantly increasing the specific gravity of a significant number of the white cells; and centrifuging the blood sample so as to separate it into a red cell layer and an adjacent white cell layer.

5. The method of claim 4 wherein the compound is one which will remove water from the individual red cells without removing significant amounts of water from the individual white cells.

6. The method of claim 4 wherein the compound is potassium oxalate.

7. A method of clarifying the interface between the red cell layer and an enhanced buffy coat cell layer in a centrifuged sample of blood comprising the step of adding to the blood sample an amount of a compound having an organic anion in combination with a freely soluble metallic cation, said amount being effective to increase the specific gravity of the red cells thereby preventing any immature red cells from being suspended in the adjacent buffy coat layer without significantly altering the specific gravity of a significant number of the buffy coat cells.

* * * * *